United States Patent [19]

Earhart et al.

[11] Patent Number: 5,318,940
[45] Date of Patent: Jun. 7, 1994

[54] CARBONLESS PAPER SOLVENT COMPRISING DIISOPROPYLBIPHENYL AND TRIISOPROPYLBIPHENYL AND PRODUCTS UTILIZING SAME

[75] Inventors: Harold W. Earhart; Gregory R. Hahn; Ronald W. Osman, all of Corpus Christi, Tex.

[73] Assignee: Koch Industries, Inc., Wichita, Kans.

[21] Appl. No.: 984,992

[22] Filed: Dec. 2, 1992

[51] Int. Cl.$^5$ ............................................. B41M 5/165
[52] U.S. Cl. ................................. 503/213; 503/215
[58] Field of Search ............. 106/21 R; 503/213, 215

[56] References Cited

U.S. PATENT DOCUMENTS

| | | | |
|---|---|---|---|
| 3,627,581 | 12/1971 | Phillips | 117/36.2 |
| 4,287,074 | 9/1981 | Earhart et al. | 585/6.3 |
| 4,699,658 | 10/1987 | Okada et al. | 106/21 |
| 4,699,659 | 10/1987 | Okada et al. | 106/21 |
| 4,774,136 | 9/1988 | Okada et al. | 428/402.2 |
| 4,795,493 | 1/1989 | Okada et al. | 106/311 |
| 4,822,767 | 4/1989 | Okada et al. | 503/213 |

FOREIGN PATENT DOCUMENTS 1352597  5/1974  United Kingdom ................ 503/213

*Primary Examiner*—B. Hamilton Hess
*Attorney, Agent, or Firm*—Shook, Hardy & Bacon

[57] ABSTRACT

A remarkably low odor carbonless paper solvent is provided comprising a mixture of diisopropylbiphenyl and triisopropylbiphenyl, generally in an amount of 50 to 90% by weight diisopropylbiphenyl and 10 to 40% by weight triisopropylbiphenyl. The solvent and a chromogenic substance such as a leuco dye are encapsulated to form microcapsules which are coated onto one surface of a carrier sheet. A color developing substance is then applied to another sheet to form a carbonless marking system. When the microcapsules are ruptured, the solubilized chromogenic substance contacts and reacts with the developer to form an image.

3 Claims, No Drawings

CARBONLESS PAPER SOLVENT COMPRISING DIISOPROPYLBIPHENYL AND TRIISOPROPYLBIPHENYL AND PRODUCTS UTILIZING SAME

BACKGROUND OF THE INVENTION

This invention relates in general to solvents for use in solubilizing dyes and, more particularly, to solvents used in the production of carbonless paper, microcapsules containing a chromogenic compound solubilized by such solvents, and pressure sensitive marking and recording material coated with such microcapsules.

Carbonless paper and other marking systems depend upon localized contact between a chromogenic compound such as a leuco dye and a color developing substance to produce a visible indicia. In such marking systems, the dye is solubilized in a solvent and the dye and solvent are then emulsified in an aqueous solution to form tiny "oil" droplets. The oil droplets are then encapsulated by the polymerization or coagulation of a suitable material to form a wall around the individual droplets.

In one application, the microcapsules which are formed can be coated on the back side of a sheet of paper or other material to form a coated back sheet. A second sheet of paper is then coated on the front side with a color developing substance, typically a proton donating component such an acidic clay or phenolic resin. The microcapsule outer walls isolate the dye from the developer until the microcapsules are ruptured by the application of localized pressure. When pressure is applied by a stylus, pen, typewriter, printer or similar instrument, the microcapsules burst and the oil solution containing the solubilized dye is released and is transferred to the second sheet of paper where the dye reacts with the acid component to form an image. Carbonless paper systems of this type are described in U.S. Pat. Nos. 3,418,656 and 3,418,250, which are incorporated by reference herein in their entirety.

Solvents which are utilized in carbonless paper systems should be capable of solubilizing the leuco dye, have a low water solubility, a viscosity which is low enough to permit the microcapsule contents to be rapidly transferred to the developer upon rupture of the microcapsule, a low or negligible odor, low volatility to reduce evaporation during processing, low toxicity, negligible health risks, and low cost. Various solvents have been identified which satisfy many of the above requirements.

The suitability of particular carbonless paper solvents is dependent upon the characteristics of the particular dyes and developers utilized. For example, a low viscosity solvent is generally required when phenolic acid developers are utilized in order to achieve rapid image development. By contrast, when using an acid clay developer, a higher viscosity solvent can be used with acceptable results.

The presence of diisopropylbiphenyl and triisopropyl-biphenyl as impurities in a solvent comprising primarily mono-isopropylbiphenyl was disclosed in U.S. Pat. No. 3,627,581 to Phillips. In that patent, it was disclosed that a mixture of isopropylbiphenyl positional isomers provides better fad resistance and print intensities in comparison to higher alkylated biphenyls such as butylbiphenyl, amylbiphenyl, hexylbiphenyl, decylbiphenyl, diisopropylbiphenyl, and triisopropylbiphenyl. It was further disclosed that a certain amount of the higher alkylated biphenyl impurities could be tolerated in the isopropylbiphenyl isomer mixture. However, when the impurities are polyisopropylbiphenyls, namely diisopropylbiphenyl with trace amounts of triisopropylbiphenyl, it was taught that they should comprise no more than 55% by weight of the total biaryl content of the solvent.

Alkylated biphenyls having up to 24 carbon atoms in the substituent alkyl groups were identified as carbonless paper solvents in U.K. Patent Publication No. 1,352,597. Diisopropylbiphenyl was specifically identified as a suitable solvent in that patent.

The use of diisopropylbiphenyl as a component in a carbonless paper solvent was also disclosed in U.S. Pat. No. 4,774,136 to Okada et al. In that patent it was disclosed that diisopropylbiphenyl could be used to prevent the crystallization of p-monoisopropylbiphenyl at low temperatures. The solvent mixture consisted essentially of (i) 30 to 80% by weight of p-monoisopropylbiphenyl or a biphenyl mixture of not less than 80% by weight of p-monoisopropylbiphenyl, not more than 20% by weight of m-monoisopropylbiphenyl and not more than 10% by weight of diisopropylbiphenyl, and (ii) 70 to 20% by weight of diisopropylnaphthalene or a specified naphthalene mixture.

A carbonless paper solvent comprising diisopropylbiphenyl and minor amounts of triisopropylbiphenyl is commercially available from Koch Chemical Company under the trademark Sure-Sol 330. The solvent comprises approximately 81.6% by weight of a mixture of diisopropylbiphenyl positional isomers and 2.3% by weight of a mixture of triisopropylbiphenyl positional isomers.

While the suitability of diisopropylbiphenyl as both a minor and a major component of a carbonless paper solvent has been recognized in the patents and commercial product discussed above, the use of triisopropylbiphenyl as other than a trace component of such a solvent has not previously been disclosed.

SUMMARY OF THE INVENTION

It is an object of this invention to provide a carbonless paper solvent that is virtually odorless but has an acceptable viscosity and is readily microencapsulated with a chromogenic material to form carbonless paper microcapsules.

It is also an object of this invention to provide a new carbonless paper solvent having acceptable odor and viscosity characteristics but which also possesses suitable dye solubilizing properties so that a uniformly mixed oil is formed within the microcapsules.

It is another object of this invention to provide a carbonless paper solvent that has a lower cost than conventional solvents and still exhibits acceptable odor, viscosity, and dye solubilizing properties.

It is a still further object of this invention to provide pressure sensitive recording or marking material which utilizes the described solvent so that desirable color developing properties are achieved.

It is a yet further object of this invention to provide carbonless paper microcapsules containing the described solvent and a chromogenic compound, which microcapsules can be used with a color developing substance to provide a pressure sensitive recording material that produces clear and dense images.

To accomplish these and other related objects of the invention, a carbonless paper solvent is provided comprising 50 to 90% by weight diisopropylbiphenyl and 7.5 to 40% by weight triisopropylbiphenyl, the balance of the solvent comprising compounds other than diisopropylbiphenyl and triisopropylbiphenyl.

In another aspect, the invention comprises microcapsules comprising a dye and a carbonless paper solvent comprising 50 to 90% by weight diisopropylbiphenyl and 7.5 to 40% by weight triisopropylbiphenyl, the balance of the solvent comprising compounds other than diisopropylbiphenyl and triisopropylbiphenyl. A secondary solvent may also be provided in the microcapsules. The secondary solvent may comprise aromatics such as linear and branched alkylbenzenes or other compounds such as linear and branched paraffins.

In yet another aspect, the invention comprises a pressure sensitive recording sheet comprising a support for carrying written or printed indicia and having coated thereon a layer of microcapsules containing a chromogenic substance and a solvent for said chromogenic substance, the solvent comprising 50 to 90% by weight diisopropylbiphenyl and 7.5 to 40% by weight triisopropylbiphenyl, the balance of the solvent comprising compounds other than diisopropylbiphenyl and triisopropylbiphenyl.

DETAILED DESCRIPTION OF THE INVENTION

In accordance with the present invention, a carbonless paper solvent is provided comprising diisopropylbiphenyl and triisopropylbiphenyl. It has been determined that a mixture of 50 to 90% by weight diisopropylbiphenyl and 7.5 to 40% by weight triisopropylbiphenyl produces a solvent which is virtually odorless but has a viscosity and other properties that make it a highly desirable carbonless paper solvent. Included within the invention are individual positional isomers of diisopropylbiphenyl and triisopropylbiphenyl. As used herein, the terms isopropylbiphenyl, diisopropylbiphenyl, and triisopropylbiphenyl include individual positional isomers as well as mixtures of two or more positional isomers of those compounds.

A preferred solvent composition comprises 50 to 80% by weight diisopropylbiphenyl and 15 to 40% by weight triisopropylbiphenyl. A more preferred composition comprises 50 to 70% by weight diisopropylbiphenyl and 20 to 30% by weight triisopropylbiphenyl. The balance of the solvent in these compositions comprises compounds other than diisopropylbiphenyl and triisopropylbiphenyl, such as alkylation products and impurities.

The solvent composition comprising diisopropylbiphenyl and triisopropylbiphenyl is used to solubilize a suitable chromogenic material in a process for making carbonless paper microcapsules. Any of various well known methods can be used for the encapsulation of the solvent and dye mixture in the microcapsules. Examples of such processes are disclosed in U.S. Pat. Nos. 3,016,308; 3,429,827; 3,578,605; 3,712,507; 3,806,463; 4,003,589; and 4,680,056, each of which is incorporated herein by reference in its entirety.

The chromogenic material useful in conjunction with the solvent of the present invention in the formation of carbonless paper microcapsules is also known as chromogenic dye-precursor material and can include any of various suitable dyes, particularly leuco dyes which produce color under acidic conditions. Such dyes may include triphenylmethanes, diphenylmethanes, xanthenes, thiazines, spiropyranes and the like. Fluorane compounds (spiroxanthenes) of the type disclosed in U.S. Pat. No. 3,920,510 are also useful as carbonless paper dyes. Examples of suitable dyes which are commercially available include Methyl Violet, Crystal Violet, Malachite green Rhodamine B, Michler's hydrol derivatives, Pergascript ® dyes, and fluorane derivatives such as One-Dye-Black 1 (ODB-1) and One-Dye-Black 2 (ODB-2). The dye may include combinations of dyes and is generally used in a concentration of 0.1-15 parts, preferably 1-8 parts, and most preferably 4-6 parts per 100 parts by weight of diisopropyl biphenyl and triisopropyl-biphenyl.

The acidic components used to develop the color of the dyes can be bentonite, zinc oxide, kaoline, clay, active clay, acid clay, zeolite, talc, colloidal silica, phenol-aldehyde resin, maleic acid-rosin resin, bis-phenol A, bis-phenol S, metal salts of organic acids, such as zinc salicylate, and the like. The acidic component is typically coated on a top surface of a sheet which underlies a first sheet having a bottom surface coated with microcapsules of the type described above. The acidic component can be coated on the sheet in a manner well known to those of skill in the art. It will be appreciated that other types of pressure sensitive recording material may be prepared using the microcapsules of the present invention.

Diisopropylbiphenyl and triisopropylbiphenyl as used in the solvent of the present invention can be made by the known Friedel-Crafts type liquid phase propylation of biphenyl, such as by alkylation of biphenyl with propylene in accordance with the process set forth in "Industrial and Engineering Chemistry Product Research and Development", Vol. 18, pages 239–241 (1969), which is incorporated herein by reference. The alkylation product produced by such process typically comprises a mixture of biphenyl, isopropylbiphenyl, diisopropylbiphenyl, triisopropylbiphenyl, and other homologous polyisopropylbiphenyls. The relative amounts of the various components in the alkylation product can be controlled by varying the molar ratio of propylene to biphenyl. Propylene to biphenyl ratios greater than 1.2:1 favor formation of larger amounts of polyisopropylbiphenyls, while ratios lower than 1.2:1 produce alkylation products which are richer in isopropylbiphenyl and biphenyl.

The alkylation product is processed to separate the diisopropylbiphenyl and triisopropylbiphenyl from the remaining components, particularly the isopropylbiphenyl. Separation can be accomplished by any suitable method such as by distillation. The yield of diisopropylbiphenyl and triisopropylbiphenyl in the distilled product is controlled by recovering a fraction having the desired boiling point range. In general, the range is selected to prevent inclusion of isopropylbiphenyl in the distillate because of the strong odor associated with all isomers of that compound. A suitable boiling point range is 603° to 629° F. or higher.

The inclusion of triisopropylbiphenyl in the carbonless paper solvent of the present invention is particularly desirable because it increases the yield of the solvent produced per distillation pass. This allows the production costs for the solvent to be lower than conventional diisopropylbiphenyl solvents while still providing the other desired properties such as low odor and acceptable viscosity.

Tetraisopropylbiphenyl and other alkylated products are typically present in minor amounts in the fraction separated from the alkylate. The separated fraction which is used in the microcapsules is primarily diisopropylbiphenyl and triisopropylbiphenyl but tetraisopropylbiphenyl and/or other alkylated products can also be present. The amounts of these other components can be chosen to modify the characteristics of the solvent and improve the economics of the solvent. Generally, it is desirable to use as much of the distillate as possible in order to maximize the overall yield.

The present solvent comprising diisopropylbiphenyl and triisopropylbiphenyl is a primary solvent. Other or secondary carbonless paper solvents can be used in the microcapsulation formulation as diluents in order to lower the overall cost of the microcapsules and/or to adjust the viscosity or other properties of the oil. These secondary solvents can be selected from aromatic solvents, including linear and branched alkylbenzenes, and other compounds such as linear paraffins, and branched paraffins. In addition, other carbonless paper solvents can be used as a diluent.

In formulating the microcapsules containing the primary solvent of the present invention, the diluent(s) can be used in the amounts of 0 to 200 parts per 100 parts of the primary solvent and preferably 11 to 100 parts per 100 parts of the primary solvent.

The following examples further exemplify the present invention and are to be read as illustrative and not in a limiting sense.

EXAMPLE 1

Alkylate Preparation

A glass lined reactor is charged with 2000 lbs biphenyl and aluminum chloride-cumene catalyst complex (0.5 wt % of $AlCl_3$ contained) and the resultant mixture is heated to 160° F. The agitated molten biphenyl/catalyst mixture is then sparged with 820 lbs propylene at a rate not to exceed reaction mixture temperature of 300° F. and head space pressure above 100 psig. After propylene addition is complete, the reaction mixture is held at 210° F. for one hour, cooled to 150° F., and then quenched with five volume percent 20° Bé caustic soda. Following refluxing for one hour, the separated organic phase is washed with water and transferred to a still.

Product Preparation

The reaction alkylate was distilled using a 72 theoretical plate Koch Engineering Co. Flexipac ® column yielding 1130 lbs of a mixture containing 81.6% diisopropylbiphenyl and 2.3% triisopropylbiphenyl by weight. Boiling point range for the carbonless paper solvent obtained was 602°-612° F. (ASTM test method D-86). The solvent produced in this example is typical of the "pure" diisopropylbiphenyl disclosed in UK 1,352,597 and that which is commercially available.

EXAMPLE 2

From distillation of a reaction alkylate, prepared in a manner similar to Example 1, 1200 lbs of a mixture comprising 75.8% diisopropylbiphenyl and 7.6% triisopropylbiphenyl by weight was obtained. ASTM test method D-86 indicated a boiling point range of 603°-616° F. for the product obtained.

EXAMPLE 3

Reaction alkylate, prepared as in Example 1, was distilled to furnish 1310 lbs of product comprising 69.3% by weight diisopropylbiphenyl and 18.8% by weight triisopropylbiphenyl. A boiling point range of 605°-620° F. was obtained for the product (ASTM D-86).

EXAMPLE 4

Distillation of reaction alkylate, described in Example 1, afforded 1420 lbs of a 63.9%/18.8% diisopropylbiphenyl/tri-isopropylbiphenyl mixture. The fluid exhibited a boiling point range of 607°-624° F. via ASTM D-86.

EXAMPLE 5

A mixture totaling 1560 lbs, comprising 58.0% diisopropylbiphenyl and 24.2% triisopropylbiphenyl, was obtained by fractionating reaction alkylate prepared as described in Example 1. ASTM test method D-86 showed a 611°-629° F. boiling point range for the product obtained.

EXAMPLE 6

To 100 parts solvent as prepared in Example 5 is added 8 parts of a Pergascript ® black dye mixture. The mixture is warmed to 100° F. and agitated to give complete solution. To the resultant solution is added 100 parts of mixed triisopropyltoluene isomers (which can be prepared by Friedel-Crafts type liquid phase propylation of toluene) and the entire solution is allowed to equilibrate. This solution, added to 150 parts aqueous solution containing 35 parts gum arabic, gives on agitation a stable suspension which, upon addition of 200 parts of a 12% gelatine solution, sufficient sodium hydroxide to maintain the pH at 9 and additional water (800 parts) gives a suspension which, upon further addition of acetic acid to pH =4 to 4.5 under agitation yields a suspension of oil microdroplets. Further addition of formaldehyde solution (4 parts $CH_2O$) and subsequent adjustment of pH to 9.65 causes hardening of the microdroplets to capsules. These microcapsules when applied by standard techniques to paper at a rate of about 5 gm/$m^2$, and dried, produced paper ready for acid development by clays or by acid resins, when broken by pressure from a stylus.

COMPARISON TEST EXAMPLE 1

Viscosities of samples prepared in the above Examples were measured using ASTM test method D-445 at 100° F. The data obtained (Table 1) illustrates an increase in viscosity as tri-isopropylbiphenyl content rises, however, all viscosities measured are acceptable, particularly for clay developer-type carbonless paper systems.

TABLE 1

| Sample | Weight % DIPB | Weight % TIPB | Viscosity (100° F., cSt) |
|---|---|---|---|
| Example 2 | 75.8 | 7.6 | 12.0 |
| Example 3 | 69.3 | 13.6 | 13.0 |
| Example 4 | 63.9 | 18.8 | 14.0 |
| Example 5 | 58.0 | 24.2 | 15.3 |

COMPARISON TEST EXAMPLE 2

Fluorane-type dyes are typically more difficult to dissolve than other dyes commonly used in carbonless copy paper systems. A 100 mL sample of solvent was heated to a constant temperature of 90° C. Small portions of a previously weighted amount of N-102 dye (Hilton Davis Co.) were added to the carrier until turbidity persisted in the sample for over one minute. The unused dye was reweighed and the difference between the original and final weights were used to calculate the solubility in grams dye per liter solvent. Examples and 5 exhibited lower solubilities of N-102 than that of the commercially available diisopropylbiphenyl (Example 1). The dye solubility of a fluid is thought to decrease with increased paraffinic character (Table 2).

TABLE 2

| Sample | Weight % DIPB | Weight % TIPB | Dye Solubility at 90° C. g N-102/L Carrier |
|---|---|---|---|
| Example 1 | 81.6 | 2.3 | 40 |
| Example 3 | 69.3 | 13.6 | 37 |
| Example 5 | 58.0 | 24.2 | 35 |

COMPARISON TEST EXAMPLE 3

Using the procedure in Comparison Test Example 2, dye solubility studies on Example 5 were also conducted on a typical multi-dye black (Ciba-Geigy mixture of Pergascripts Orange I-5R (11%), Red I-6B (15%), Blue I-2R (7%), Blue S-RB (15%), and Green I-26N (52%)) and a blue dye (Pergascript Blue I-2R) commonly used for black and blue developed images in carbonless paper systems employing acid clay developers. The solvent of Example 5 exhibited acceptable solubilizing power, in ranges typical of other commercially available carbonless paper solvents, despite its high triisopropylbiphenyl content (Table 3).

TABLE 3

| Sample | Leuco Dye | Dye Solubility at 90° C. g N-102/L Carrier |
|---|---|---|
| Example 5 | Hilton Davis N-102 | 35 |
| Example 5 | Pergascript Mixture | 180 |
| Example 5 | Pergascript Blue I-2R | 65 |

COMPARISON TEST EXAMPLE 4

A sample of each solvent was placed in a clean, odor-free brown glass bottle and labeled randomly as A, B, C, etc. Odor panel participants were allowed to smell each sample and indicate on a response form their grade for each carrier, with strength of odor increasing from 1 to 5 (Table 4). Despite the presence of triisopropylbiphenyl contained in Example 5, the odor was surprisingly difficult to distinguish from that of distilled water. Additionally, the odor was found notably lower than that of commercially available solvents with reported low odor.

TABLE 4

| Sample | Strength of Odor | | | | | Average Score |
|---|---|---|---|---|---|---|
| | 1 | 2 | 3 | 4 | 5 | |
| distilled water | 7 | 1 | 0 | 0 | 0 | 1.1 |
| Example 5 | 2 | 6 | 0 | 0 | 0 | 1.8 |
| diisopropylnaphthalene | 0 | 0 | 6 | 0 | 2 | 3.5 |
| p-isopropylbiphenyl, 93% | 0 | 0 | 1 | 4 | 3 | 4.3 |

COMPARISON TEST EXAMPLE 5

Following the procedure described in Comparison Test Example 4 above, a sample of commercially available diisopropylbiphenyl (Example 1) and Example 5 were compared with commercially available butylbiphenyl and distilled water using a randomly chosen group of 40 people (Table 5). Again, the odor of Example 5 compared favorably with that of both distilled water and Example 1. Example 1, commercially available diisopropylbiphenyl, is recognized in the carbonless paper industry as being essentially odor-free.

TABLE 5

| Sample | Strength of Odor | | | | | Average Score |
|---|---|---|---|---|---|---|
| | 1 | 2 | 3 | 4 | 5 | |
| Example 1 | 27 | 6 | 2 | 3 | 2 | 1.7 |
| Example 5 | 19 | 11 | 8 | 1 | 1 | 1.9 |
| butylbiphenyl | 2 | 5 | 5 | 10 | 18 | 3.9 |
| distilled water | 25 | 9 | 5 | 1 | 0 | 1.6 |

COMPARISON TEST EXAMPLE 6

In a manner similar to the odor evaluation in Comparison Test Example 5, the odors of Examples 1–5 were compared with each other and that of commercially available diisopropylnaphthalene (Table 6). Data from 22 randomly chosen participants illustrated little variation in odor from Examples 1–5, indicating that solvents which include triisopropylbiphenyl were essentially odor-free.

TABLE 6

| Sample | Strength of Odor | | | | | Average Score |
|---|---|---|---|---|---|---|
| | 1 | 2 | 3 | 4 | 5 | |
| Example 1 | 14 | 7 | 3 | 2 | 0 | 1.9 |
| Example 2 | 14 | 7 | 0 | 0 | 1 | 1.5 |
| Example 3 | 17 | 2 | 2 | 0 | 1 | 1.5 |
| Example 4 | 10 | 8 | 4 | 0 | 0 | 1.7 |
| Example 5 | 9 | 8 | 3 | 2 | 0 | 1.9 |
| diisopropylnaphthalene | 0 | 2 | 7 | 4 | 9 | 3.9 |

Having thus described the invention, what is claimed is:

1. A recording sheet comprising a support for carrying written or printed indicia having coated thereon a continuous layer of microcapsules containing a chromogenic substance and a solvent for said substance, said solvent comprising diisopropylbiphenyl and triisopropylbiphenyl, the triisopropylbiphenyl being present in an amount of 7.5 to 40% by weight based on the total weight of the solvent.

2. The recording sheet as set forth in claim 1, wherein said solvent comprises 50 to 90% by weight diisopropylbiphenyl.

3. The recording sheet as set forth in claim 1, wherein said solvent comprises 50 to 70% by weight diisopropylbiphenyl and 20 to 30% by weight triisopropylbiphenyl.

* * * * *